United States Patent [19]

Ramsner et al.

[11] Patent Number: 4,779,466
[45] Date of Patent: Oct. 25, 1988

[54] METHOD AND APPARATUS FOR CONTINUOUSLY TAKING A HOT GAS SAMPLE TO BE ANALYZED FROM A REACTION CHAMBER

[75] Inventors: Wolfgang Ramsner, Haidershofen; Karl Ruemer, Linz; Kurt Hölzl, Sarleinsbach, all of Austria

[73] Assignee: Voest-Alpine Aktiengesellschaft, Linz, Austria

[21] Appl. No.: 30,151

[22] Filed: Mar. 25, 1987

[30] Foreign Application Priority Data

Apr. 29, 1986 [EP] European Pat. Off. ........ 86890119.0

[51] Int. Cl.$^4$ .......................... G01N 1/26; G01N 1/24
[52] U.S. Cl. .............................. 73/863.33; 73/863.12; 73/863.24; 73/863.86; 73/863.83
[58] Field of Search ........... 73/863.11, 863.12, 863.23, 73/863.24, 863.81, 863.33, 863.31, 863.25, 863.83, 863.84, 863.86, 864.73, 863.82, 863.85, 864.74; 422/119

[56] References Cited

U.S. PATENT DOCUMENTS

| | | |
|---|---|---|
| 3,748,906 | 7/1973 | Manka . |
| 4,272,481 | 6/1981 | Ahlstrom, Jr. et al. ............. 422/62 |
| 4,485,684 | 12/1984 | Weber et al. ................ 73/863.11 X |

FOREIGN PATENT DOCUMENTS

| | | |
|---|---|---|
| 95802 | 12/1983 | European Pat. Off. . |
| 24877 | 3/1978 | Japan ................................ 73/863.24 |

*Primary Examiner*—Tom Noland
*Attorney, Agent, or Firm*—Kurt Kelman

[57] ABSTRACT

In order to ensure that a sample can be taken continuously from a reaction chamber with a minimum of maintenance work, the sample gas is extracted from the reaction chamber in two identical extraction lines in alternation and at a rate which exceeds the rate required for the analysis and surplus gas which has been extracted by one extraction line is branched from the sample gas and is blown back to the reaction chamber through the other extraction line.

12 Claims, 2 Drawing Sheets

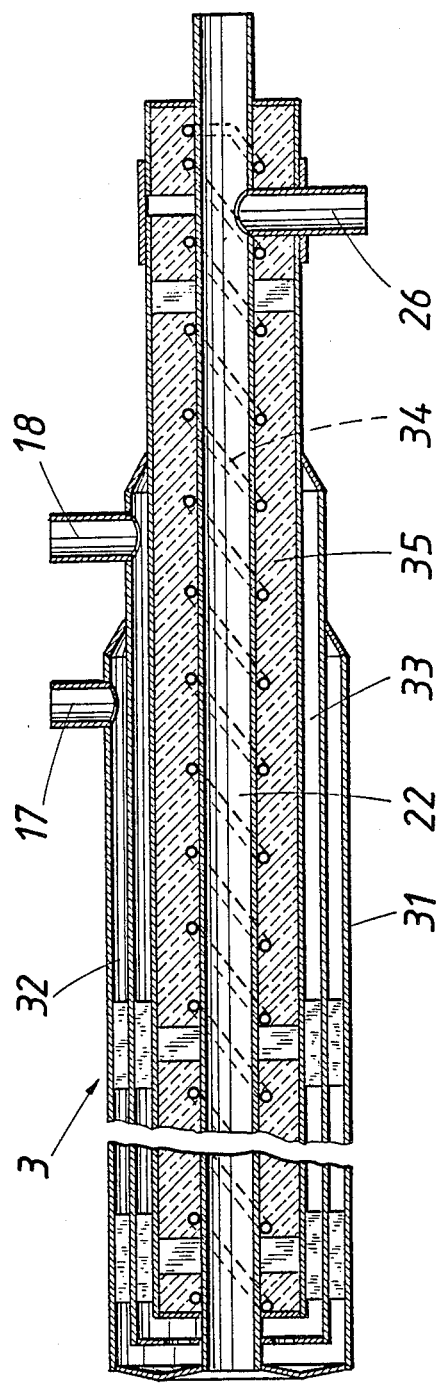

METHOD AND APPARATUS FOR CONTINUOUSLY TAKING A HOT GAS SAMPLE TO BE ANALYZED FROM A REACTION CHAMBER

BACKGROUND OF THE INVENTION

1. Field of the Invention

This invention relates to a method for continuously taking a hot sample gas to be analyzed from a reaction chamber, wherein the sample gas is taken by means of an extraction probe and is delivered to an analyzer through an extraction line comprising at least one filter, and to apparatus for carrying out the method.

2. Description of the Prior Art

For the control of a process in dependence on the composition of the gases formed in the process, sample gas must be taken from the reaction chamber and must be delivered to an analyzer. This will be particularly difficult if the gas is hot and laden with gas, such as is the case with gases which are formed by the calcination of a ground raw mixture of raw materials in the production of cement. In that case the gas temperature in the reaction chamber are so high that the extraction probes used to take the sample gas from the reaction chamber must be cooled so that the temperature along the extraction line may fall below the dew point temperature. In that case the condensate and the entrained dust particles may form a sludge, which deposits in the extraction probe and in the filter that is connected to the extraction probe so that the deposits may restrict or block the flow paths for the sample gas. For this reason, clean-up operations are periodically required to remove the deposits from the extraction line and to clean the filter which precedes the analyzer. Such clean-up operations involve a substantial expenditure and have also the disadvantage that no gas sample can be taken from the reaction chamber during the clean-up operation so that the process cannot be controlled during that time. Besides, the gas at a relatively low rate is required for the analysis so that the sample gas takes a relatively long time to flow along the flow paths provided from the reaction chamber to the analyzer and, as a result, any change in the gas composition can be taken into account in the process control only with a substantial time lag.

SUMMARY OF THE INVENTION

It is an object of the invention to avoid said disadvantages to provide for the continuous taking of hot sample gas from a reaction chamber a method in which the risk of a restriction or clogging of the flow paths for sample gas is substantially avoided and any maintenance work which will be required will not involve an interruption of the taking of the sample. Besides, the response time of the process control should be substantially shortened.

That object is accomplished in accordance with the invention in that the sample gas is extracted from the reaction chamber in two identical extraction lines in alternation and at a rate which exceeds the rate required for the analysis and surplus gas which has been extracted by one extraction line is branched from the sample gas and is blown back to the reaction chamber through the other extraction line.

Because surplus gas which has been extracted is returned through the extraction line which is not used to extract sample gas at a time, that extraction line is blown through opposite to the direction of flow of the sample gas being extracted so that that extraction line is cleaned and any dust which has been retained in the filter is detached from the filter and is returned to the reaction chamber through the extraction probe. Because the two extraction lines are used in alternation to extract sample gas, said extraction lines are automatically cleaned in alternation and maintenance work will be only rarely required. When it is desired to blow out an extraction line with compressed air, this will not interfere with the continuous taking of the sample gas because the sample gas can be extracted from the reaction chamber through the extraction line which is not being blown out with compressed air. In that case the surplus gas which has been extracted is not recycled to the reaction chamber but is blown off. When one extraction line has separately been blown out with compressed air, that extraction line may initially be purged with surplus gas from the other extraction line so that the result of the analysis will not be falsified by a presence of residual compressed air in the extraction line that has been blown out with compressed air.

The extraction of gas at a rate which is higher than is required for the analysis affords also the advantage that the extraction probes may be larger in diameter so that the gas will flow at a lower velocity in the extraction probe, a considerable part of the dust content of the sample gas can deposit in the extraction probes and the load on the filters downstream of the extraction probes will be substantially decreased. Contrary to the conventional taking method a deposition of dust adjacent to the extraction probes is not detrimental in the present method because said deposited dust will be returned into the reaction chamber as the extraction probes air back-purged with the surplus gas that has been taken.

Because gas sample is taken at a higher rate, the time required for the flow of the gas from the reaction chamber to the analyzer will be reduced so that the process control will respond more quickly to changing process conditions.

Within the scope of the invention the surplus gas which has been extracted may be branched off when all gas which has been extracted has been cooled and the resulting condensate has been drained from gas sample, and the branched off surplus gas is then returned to the reaction chamber. In that case a dry gas will be available for back-purging the other extraction line and said dry gas can absorb moisture which may have accumulated in that extraction line during its previous use to extract a sample. This drying will assist the cleaning of the extraction lines and will eliminate the risk of an agglomeration of deposited dust particles.

The process may be carried out by means of an apparatus which comprises a gas analyzer that is connected to a reaction chamber by means of an extraction line that comprises an extraction probe and at least one filter. In accordance with the invention such an apparatus differs from the conventional apparatus of the same type that a second extraction line also comprising an extraction probe and at least one filter is connected to the reaction chamber in parallel to the first-mentioned extraction line, change-over valve means are provided for connecting the two extraction lines in alternation to a feed line that is connected to the analyzer and incorporates a feed pump, and the feed line has connected to it on the pressure side of the feed pump two return lines, each of which contains at least one pressure relief valve and is adapted to be shut off and leads to one of the extraction lines.

By means of the change-over valve means the extraction lines can be connected to the analyzer in alternation. The feeding of gas is ensured by the feed pump, which is incorporated in the feed line between the change-over valve means and the analyzer and which will deliver gas at a rate in excess of the rate required for the analysis. The surplus gas is forced back through a pressure relief valve and the return line connected to the feed line to that extraction line which is not connected to the analyzer at a given time so that said extraction line is cleaned by being back-purged by the surplus gas which has been taken.

When one of the two extraction lines is to be blown out with compressed air, the surplus gas which has been extracted must not be returned to the extraction line that is to be blown out with compressed air. For this purpose the feed line may have connected to it via a pressure relief valve a blow-off line, which is adapted to be shut off and which can be opened when the associated extraction line is to be blown out with compressed air. As the blow-off line is opened, the associated return line is shut off at the same time.

Because in the taking of hot sample gas the extraction probe must be protected at its outside surface from an excessively high temperature by an adequate cooling, the temperature in the extraction line might drop below the dew point temperature of the sample gas. Whereas that danger is lower than in the known methods because sample gas is taken at a higher rate, that danger can be reliably eliminated in spite of the cooling of the outside surfaces of the extraction probe merely in that the two extraction lines are heated by heating means to a temperature above the dew point temperature of the gas sample.

In that case the sample gas which has extracted from the reaction chamber by one of the two extraction lines is desirably cooled in a cooler, which is incorporated in the feed line on the suction side of the feed pump so that it is sufficient to associate with both extraction lines a single cooler provided with a condensate drain.

BRIEF DESCRIPTION OF THE DRAWING

FIG. 2 is an axial sectional view showing on an enlarged scale one of the two extraction probes of the apparatus of FIG. 1.

DETAILED DESCRIPTION OF THE PREFERRED EMBODIMENT

Figure 1:
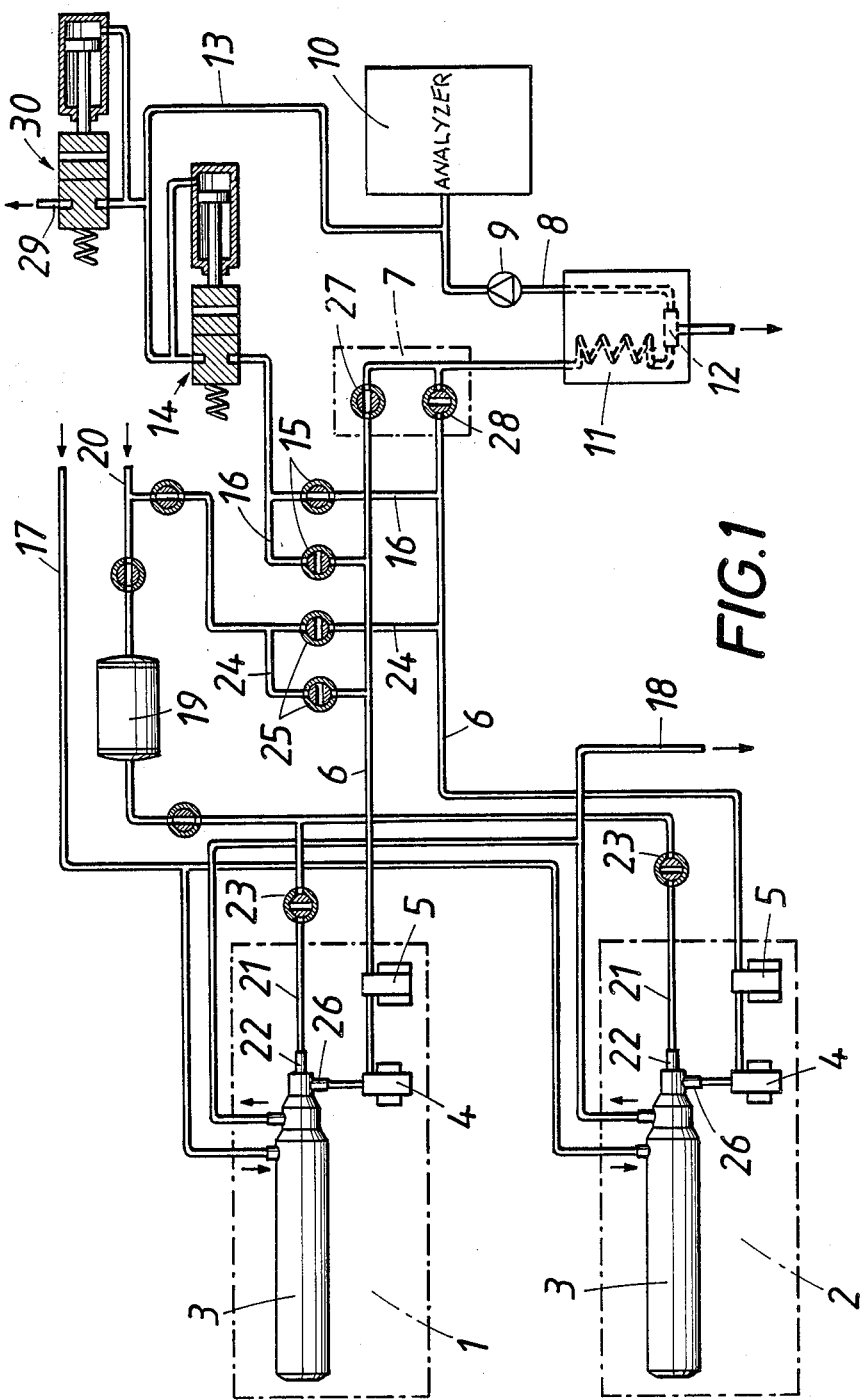
FIG. 1 is a diagrammatic block circuit diagram showing apparatus for a continuous taking of a hot gas sample.

Two identical extraction lines 1 and 2 are provided for taking a gas sample from a reaction chamber that is not shown. Downstream of the extraction probe 3, each of the extraction lines 1 and 2 comprises an extraction probe 3 and two filters, namely, a coarse filter 4 and a fine filter 5. Each of the extraction lines 1 and 2 comprises a gas line 6 connecting the fine filter 5 via change-over valve means 7 to a common feed line 8, which incorporates a feed pump 9 for delivering the sample gas to an analyzer 10. On the suction side of the feed pump 9 the feed line incorporates a cooler 11, which is provided with a condensate drain 12. On the discharge side of the feed pump 9 a connecting line 13 provided with a pressure relief valve 14 branches from the feed line 8 and behind the valve 14 branches into two return lines 16, which lead to respective ones of the two gas lines 6 and each of which can be shut off by a valve 15.

A supply line 17 and a return line 18 for liquid coolant are provided for cooling the outside surface of the extraction probes 3. Besides, the extraction probes 3 can be blown out with compressed air flowing opposite to the direction in which samples are taken. For that purpose a compressed-air reservoir 19 is provided, which can be supplied with compressed air via a compressed air line from a compressed air source, not shown. That compressed air reservoir is connected by blast lines 21 to the gas-conducting inner tubes 22 of the extraction probes 3. Said blast lines 21 can be opened by means of valves 23. As is apparent from FIG. 2 the arrangement is such that the blow-out air flows coaxially into the inner tube 22 of the extraction probe 3 and thus effects a desirable cleaning. To permit the filters 4 and 5 to be blown out with compressed air, the compressed air line 20 is connected by two connecting lines 24 to respective ones of the gas lines 6. Each connecting line 24 contains a compressed air valve 25. When one of the shut-off valves 25 is opened, the compressed air is initially forced through the fine filter 5 and then through the coarse filter 4 opposite to the direction of gas flow from the reaction chamber and the compressed air will subsequently flow through the outlet line 26 of the extraction probe 3 into the inner tube 22 of that probe and from the inner tube into the reaction chamber.

The sample gas is taken from the reaction chamber through the two extraction lines 1 and 2 in alternation and is delivered via the change-over valve means 7 to the analyzer 10. For instance, when the gas sample is extracted through the extraction line 1, the gas line 6 of that extraction line is connected by the change-over valve means 7 to the feed line 8 in that the valve 27 of the change-over valve means 7 is opened and the valve 28 in the gas line 6 of the extraction line 2 is closed. The sample gas now enters the cooler 11, from which the resulting condensate is drained so that the gas sample is dry as it is entering the analyzer 10. Because gas has been taken from the reaction chamber at a higher rate than is required for the analysis, the surplus gas is returned to the gas line 6 of the extraction line 2. For that purpose the surplus gas flows through the pressure relief valve 14, which is incorporated in the connecting line 13, and through one of the two return lines 16, which leads to the gas line 6 of the extraction line 2 and is opened for that purpose by the shut-off valve 15. The other valve 15 is closed at the same time to shut off the other return line 16, which leads to the gas line 6 of the extraction line 1. As a result, the surplus gas that is not required for the analysis is first forced through the fine filter 5 and then through the coarse filter 4 opposite to the direction of flow of the sample gas and then enters through the probe 3 of the extraction line 2 the reaction chamber. By that back-purging the extraction line 2 is cleaned to remove deposited and retained solid particles. When the extraction line 2 has thus been cleaned the change-over valve means 7 and the valves 15 in the return lines 16 can be actuated so that sample gas is now extracted through the cleaned extraction line 2 and the other extraction line is cleaned by the surplus gas.

When it is desired in spite of said cleaning to blow out one of the two extraction lines with compressed air, the continuous taking of the sample need not be interrupted for that blow-out because the extraction of the sample can be continued through the other extraction line. When it is desired to blow out, e.g., the extraction line 1 with compressed air the shut-off valve 15 in the return line 16 leading to the gas line 6 of the extraction line 1 is opened to permit the filters 5 and 4 to be blown out with compressed air. After a suitable blow-out time the valve 23 in the blast line 21 associated with the extraction line 1 is opened and compressed air is blown through the inner tube 22 of the extraction probe 3 so that the detaching of dust particles which have been retained by the filters 4 and 5 will not be disturbed by the compressed air flowing from line 21 opposite to the air blast from gas line 6. When the extraction line 1 has been blown out with compressed air, the valves 23 and 25 are closed and the valve 15 is opened and the blowoff line 29 is subsequently closed so that the lines, the filter 4 and 5 and the extraction probe can be purged by the surplus sample gas and any compressed air contained therein will be blown by the surplus sample gas into the reaction chamber and when the sample is subsequently extracted via the extraction line 1 the result of the analysis will not be falsified by a content of compressed air. The extraction line 2 is blown out in a similar manner.

Because the gas sample must be taken from a hot reaction chamber, the outside surfaces of the extraction probes must be cooled in order to prevent excessively high temperatures. For that purpose the inner tube 22 is surrounded by a twopart cooling jacket 31, which in its outer annular gap 32 conducts a liquid coolant, usually water, which is then reversed and withdrawn through an inner annular gap 33 in countercurrent operation. But such a cooling of the jacket 31 of the extraction probe might result in a temperature drop below the dew point temperature. This is avoided in that the inner tube 22 is heated by an electric resistance heater 34 to a temperature above the dew point temperature of the sample gas. The inner tube 22 is heat-shielded by a heat insulation 35 from the cooled jacket 31. Owing to that special measure the temperature profile along the cooling jacket is not critical because even if the liquid coolant assumes a temperature below the dew point temperature of the gas a condensation in the inner tube 22 will be prevented by the heating of the inner tube.

We claim:

1. In a method of continuously taking hot sample gas from a reaction chamber and for delivering said sample gas at a predetermined rate to an analyzer wherein said sample gas is conducted in an extracting direction in an extraction line comprising an extraction probe and filter means downstream of said probe, the improvement residing in the gas is extracted from said reaction chamber at a rate in excess of said predetermined rate through two identical extraction lines in alternation, each of which extraction lines contains an extraction probe and filter means downstream of said probe, and surplus gas in one of said extraction lines in excess of said predetermined rate is diverted from said sample gas downstream of said filter means in said one extraction line and is blown back into the reaction chamber through the other extraction line in a direction which is opposite to said extracting direction.

2. The improvement set forth in claim 1, wherein all gas which has been extracted in each of said extraction lines is cooled with formation of condensate, said condensate is removed from said gas and said surplus gas is diverted from said sample gas after the condensate has been removed therefrom.

3. The improvement set forth in claim 2, wherein each of said extraction probes is cooled in a portion disposed near the outside surface of said probe, and each of said extraction lines is heated while it is extracting sample gas in order to maintain the sample gas in said extraction line at a temperature above the dew point temperature of said sample gas.

4. The improvement set forth in claim 3, wherein each of said extraction lines while extracting sample gas is heated at its extraction probe radially inwardly of said portion which is disposed near the outside surface of said probe.

5. The improvement set forth in claim 1 wherein each of said extraction probes is cooled in a portion disposed near the outside surface of said probe, and each of said extraction lines is heated while it is extracting sample gas in order to maintain the sample gas in said extraction line at a temperature above the dew point temperature of said sample gas.

6. The improvement set forth in claim 5, wherein each of said extraction lines while extracting sample gas is heated at its extraction probe radially inwardly of said portion which is disposed near the outside surface of said probe.

7. In apparatus for continuously taking a hot sample gas to be analyzed from a reaction chamber, which apparatus comprises an extraction line comprising an extraction probe and filter means downstream of said probe, the improvement comprising a feed line for delivering said sample gas to be analyzed, a second extraction line comprising a second extraction probe and a second filter means downstream of the second probe which also takes hot sample gas from the reaction chamber, change-over valve means for connecting said two extraction lines downstream of each of said filter means to said feed line in alternation, return lines, which branch from said feed line and are connected to respective ones of said extraction lines between respective ones of said filter means and said change-over valve means, and a shut-off valve incorporated in each of said return lines.

8. The improvement set forth in claim 7, wherein a feed pump having a suction side connected to said change-over valve means and having a discharge side is incorporated in said feed line and said return lines branch from said feed line downstream of the discharge side of said feed pump.

9. The improvement set forth in claim 8, wherein a pressure relief valve is associated with each of said return lines.

10. The improvement set forth in claim 8, wherein a blow-off line is connected to said feed line downstream of said feed pump and a pressure relief valve is associated with said blow-off line.

11. The improvement set forth in claim 7, wherein heating means are associated with each of said extraction lines for heating each one to a temperature above the dew point temperature of the gas being extracted therethrough.

12. The improvement set forth in claim 7, wherein each of said extraction probes is provided with cooling means in a portion disposed near the outside surface thereof and with heating means for maintaining said gas being extracted through said extraction line connected thereto at a temperature above the dew point temperature of said sample gas.

* * * * *